(12) United States Patent
Chao

(10) Patent No.: US 8,569,372 B2
(45) Date of Patent: Oct. 29, 2013

(54) METHOD FOR PREVENTING OR TREATING A DISEASE, DISORDER OR CONDITION INDUCED BY RETINA ISCHEMIA

(75) Inventor: Hsiao-Ming Chao, Taipei (TW)

(73) Assignees: Hsiao-Ming Chao, Taipei (TW); Chieh-Cheng Ke, Taipei (TW)

( * ) Notice: Subject to any disclaimer, the term of this patent is extended or adjusted under 35 U.S.C. 154(b) by 99 days.

(21) Appl. No.: 13/246,057

(22) Filed: Sep. 27, 2011

(65) Prior Publication Data

US 2013/0079411 A1    Mar. 28, 2013

(51) Int. Cl.
*A61K 31/19* (2006.01)
(52) U.S. Cl.
USPC .......................................................... 514/557

(58) Field of Classification Search
USPC .......................................................... 514/557
See application file for complete search history.

(56) References Cited

U.S. PATENT DOCUMENTS 7,851,501 B2 * 12/2010 Aydt et al. ..................... 514/438

OTHER PUBLICATIONS

Saravanan et al., Phytomedicine, 2010, 17(14): 1086-1089.*
Tsujikawa et al., Am. J. Physiology, 2000, 279(3,Pt. 2):R980-R989.*

* cited by examiner

*Primary Examiner* — Rei-tsang Shiao
(74) *Attorney, Agent, or Firm* — WPAT, P.C.; Anthony King

(57) ABSTRACT

The present invention provides a method for preventing or treating a disease, disorder or condition induced by retina ischemia, comprising administering to a subject in need thereof a S-allyl-L-cysteine in a therapeutically effective amount.

8 Claims, 5 Drawing Sheets

METHOD FOR PREVENTING OR TREATING A DISEASE, DISORDER OR CONDITION INDUCED BY RETINA ISCHEMIA

FIELD OF THE INVENTION

The present invention relates to a use of S-allyl-L-cysteine in preventing or treating a disease, disorder or condition induced by retina ischemia.

BACKGROUND OF THE INVENTION

Central/branch retinal artery/vein occlusion, diabetes, glaucoma and, possibly, age related macular degeneration (AMD) are conditions associated with retinal ischaemia. All these diseases may lead to severe sequelae. Therefore, the management of retinal ischaemia is crucial.

After ischaemia/reperfusion (I/R), large amounts of reactive oxygen species (ROS) such as $H_2O_2$ are produced. These ROS attack nearby cells and cause tissue damage. Moreover, excessive release of excitatory transmitters such as the glutamate from ischaemia affected neurons leads to neuronal overstimulation and unwanted depolarisation. Consequently, neurons that possess a high density of glutamate receptors are most at risk. This explains why neurons such as retinal ganglion cells (RGCs) and amacrine cells, as well as their neuronal processes, which are located in the inner retina, are vulnerable to (I/R).

Ischaemia induces angiogenesis. Furthermore, in the retina, angiogenesis is often disorganized and typically results in oedema and haemorrhage; these have adverse effects on visual function. There is an urgent need for therapies that promote endogenous protective responses and prevent harmful angiogenesis. Increased levels of hypoxia-inducible factor-1Alpha (HIF-1 Alpha) have been found to be present after retinal ischaemia. HIF-1 binds to the hypoxia response element in hypoxia-responsive target genes, and triggers the expression of vascular endothelium growth factor (VEGF) and matrix metalloproteinases (MMPs). Liu et al. have shown that oxidative stress in human retinal pigment epitheliums (hRPEs) results in up-regulation of VEGF and MMP-9. Additionally, ischaemia has been proved to result in irreversible RGC loss that is accompanied by MMP-9 up-regulation. All the above evidence suggests that the over-expression of HIF-1 Alpha, VEGF and/or MMP-9 in the retina or in RGCs is directly related to ischaemic/ischaemic-like insult, but the relationship in more detail is unknown.

S-allyl L-cysteine (SAC), an active organosulfur compound in aged garlic extract, has been reported to possess antioxidative activity. In macrophages and endotheliums, SAC has been shown to exhibit potent antioxidative effects involving the scavenging of superoxide radicals, hydroxyl radicals and hydrogen peroxide.

SUMMARY OF THE INVENTION

Figure 1:
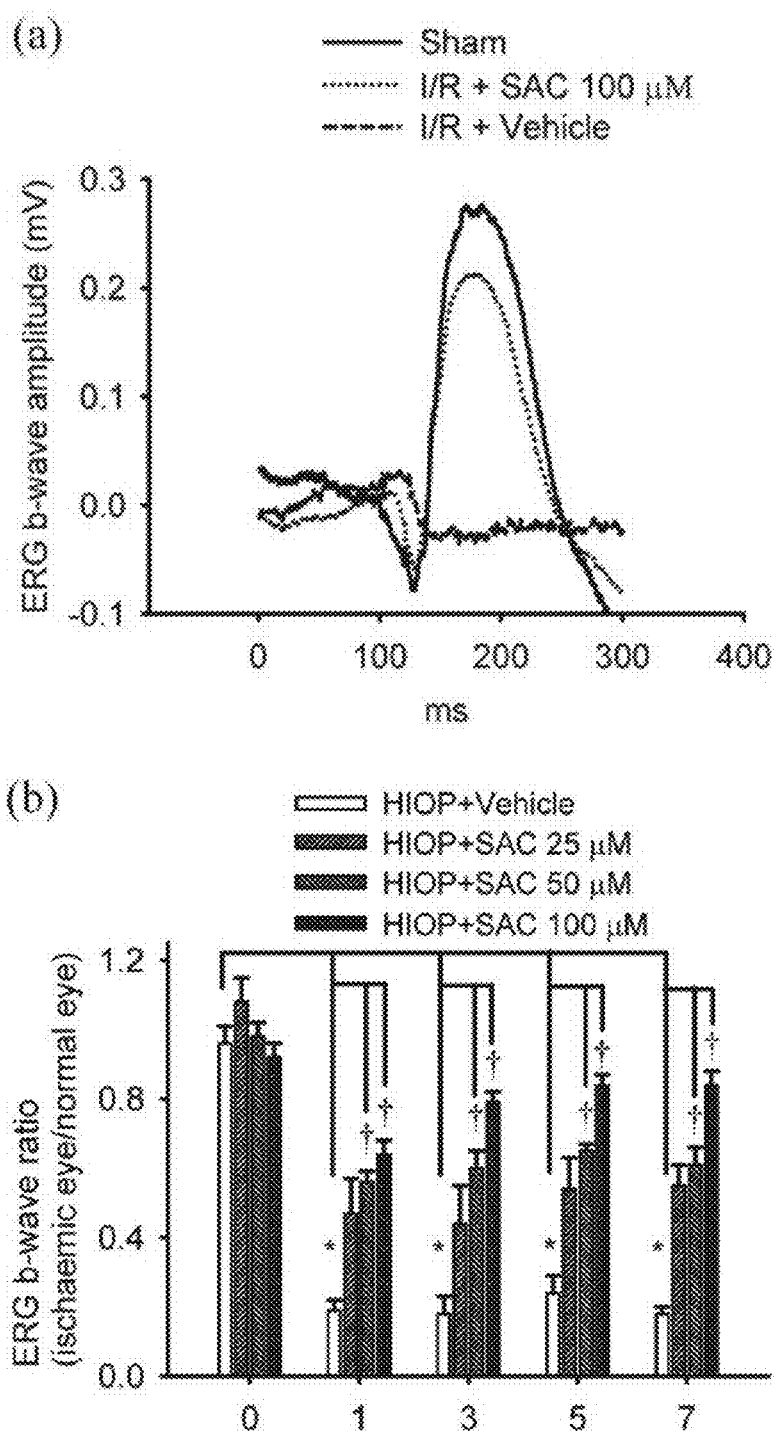
FIG. 1 shows: (a) ERG analysis of a sham-operated eye (normal control), and an ischaemic eye treated with vehicle (0.9% saline) or SAC, showing the a- or b-wave amplitude. The ERG b-wave amplitude was drastically decreased after high IOP induced retinal ischaemia/reperfusion (I/R) for 1 day. This decrease was not influenced by pretreatment with vehicle. Pretreatment with 100 μM SAC effectively alleviated the effect of retinal ischaemia and the reduction in b-wave amplitude was dramatically improved. (b) Summary of results showing the effects of 15-minute pretreatment with intravitreous SAC on rats that underwent retinal I/R. As compared to the pre-ischaemic ERG b-wave amplitude (ratio) baseline, there was a significant b-wave reduction (*$p<0.05$) in the vehicle-pretreated ischaemic retina at 1, 3, 5 and 7 days after ischaemia/reperfusion. As compared to the ischaemic eyes pre-treated with vehicle, pretreatment with 25 μM, 50 μM or 100 μM of SAC dose-dependently and significantly attenuated ischaemia induced reduction (at 50 μM and 100 μM; †$p<0.05$) in ERG b-wave amplitudes. The results are the mean±standard error of the mean for six animals (n=6). The abbreviations are: ERG, electroretinogram; IOP, intraocular pressure; SAC, S-allyl L-cysteine.

The present invention relates to a method for preventing or treating a disease, disorder or condition induced by retina ischaemia, comprising administering to a subject in need thereof a S-allyl-L-cysteine in a therapeutically effective amount.

DETAILED DESCRIPTION OF THE INVENTION

In the present in vitro study, ischaemic-like injury, namely oxidative stress due to $H_2O_2$ in retinal ganglion cell-5 (RGC-5) cells is induced. The present study investigates whether and by what mechanisms SAC is able to protect against retinal ischaemia. Acutely raising the IOP of a rat's eye, followed by reperfusion, is known to cause physiological dysfunction, and the death of cholinergic amacrine cells. The former is assessed by measuring changes in electroretinogram (ERG) b-wave amplitude. The latter is explored by analyzing the effect of SAC on damage to the inner retina involving amacrine cells. In addition, changes in the levels of Thy-1, HIF-1 Alpha, VEGF or MMP-9 at both mRNA and protein levels were also investigated.

Retinal ischaemia associated ocular disorders are vision-threatening. The aim of the present study was to examine whether S-allyl L-cysteine (SAC) is able to protect against retina ischaemia/reperfusion (I/R) injury.

The present invention demonstrates that ischaemia and/or ischaemic-like insult significantly affected the retina and cultured RGC-5 cells electrophysiologically, immunohistochemically, in terms of cell viability, and in terms of molecular biology. It is of clinical importance that all these changes, which follow ischaemia to the retina and/or ischaemic-like insult to the RGC-5 cells, are significantly attenuated by pre-treatment with SAC. The present invention is the first study to prove that SAC is able to protect the retina against ischaemia and/or ischaemic-like insult by acting as an antioxidant, while also acting to suppress the up-regulation of HIF-1 Alpha, VEGF and MMP-9 that occurs under these conditions. Both retinal ischaemia and neovascular AMD have been shown to be associated with an up-regulation of VEGF and MMP-9, which are presumed to be downstream mediators of ischaemia/hypoxia-related HIF-1 Alpha. Thus, SAC is potentially useful when managing bothersome retinal ischaemia events such as defined central/branch retinal artery/vein occlusion, and the intractable wet AMD.

In summary, the present invention proves that retinal ischaemia induces in rats various characteristic changes, including electrophysiological dysfunction (ERG b-wave), cholinergic amacrine cell body/neuronal process loss (ChAT immunoreactivity), down-regulation in Thy-1 mRNA (indexing RGCs), and up-regulation of HIF-1 Alpha/VEGF/MMP-9 mRNA. These results are paralleled by similar results for RGC-5 cells, where an insult by $H_2O_2$ up-regulates HIF-1 Alpha, VEGF and MMP-9 expression and causes RGC-5 cell death. These detrimental effects were significantly blunted by pre-treatment with SAC. The above findings strongly support the hypothesis that SAC is able to protect against retinal ischaemia by, at least in part, acting as an antioxidant and also as a down-regulator of the defined I/R related up-regulation of HIF-1 Alpha, VEGF and/or MMP-9.

Therefore, the present invention provides a method for preventing or treating a disease, disorder or condition induced by retina ischemia, comprising administering to a subject in need thereof a S-allyl-L-cysteine in a therapeutically effective amount.

All the compounds presented in the present invention may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; Alpha- and Beta-forms; axial and equatorial forms; boat-, chair-, twist-, envelope- and halfchair-forms; and combinations thereof, hereinafter collectively referred to as "isomers" (or "isomeric forms").

If the compound is in crystalline form, it may exist in a number of different polymorphic forms.

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Unless otherwise specified, the compounds of the present invention include all such isomeric forms, including (wholly or partially) racemic and other mixtures thereof. Methods for the preparation (e.g., asymmetric synthesis) and separation (e.g., fractional crystallization and chromatographic means) of such isomeric forms are either known in the art or are readily obtained by adapting the methods taught herein, or known methods, in a known manner.

In a preferred embodiment, the disease, disorder or condition induced by retina ischemia is retina ischemia, retina ischemia, central/branch retinal artery/vein occlusion, diabetes, glaucoma or age related macular degeneration (AMD).

In a preferred embodiment, the S-allyl-L-cysteine attenuates the ischaemia induced reduction in electroretinogram b-wave amplitude.

In a preferred embodiment, the S-allyl-L-cysteine attenuates the retina ischemia induced decrease in Thy-1 mRNA indexing retinal ganglion cells.

In a preferred embodiment, the S-allyl-L-cysteine attenuates the HIF-1 Alpha mRNA increase induced by retina ischemia.

In a preferred embodiment, the S-allyl-L-cysteine attenuates the VEGF mRNA increase induced by retina ischemia.

In a preferred embodiment, the S-allyl-L-cysteine attenuates the MMP-9 mRNA increase induced by retina ischemia.

In a preferred embodiment, the S-allyl-L-cysteine protects retinal ganglion cell-5 against oxidative stress. Preferably, the oxidative stress is induced by $H_2O_2$.

The present invention also provides a method for preventing or treating a disease, disorder or condition induced by retina ischemia, comprising administering to a subject in need thereof a composition comprising S-allyl-L-cysteine in a therapeutically effective amount.

The compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The compositions of the invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, compositions for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The intravitreous injection form is the same as the one of Lucentis. The compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

EXAMPLES

The examples below are non-limiting and are merely representative of various aspects and features of the present invention.

Example 1

Methods
Animals

All investigations involving the use of animals conformed to the Association for Research in Vision and Ophthalmology Statement for the Use of Animals in Ophthalmology and Vision Research and were approved by the Institutional Review Board of Cheng Hsin General Hospital (Taipei, Taiwan). The six-week-old Wistar rats were kept in an animal house where the humidity was 40-60% and the temperature 19-23° C. They were kept on a 12-hour light/dark cycle with 12 to 15 air changes/hour. The animals were provided with food and water ad libitum.

Analgesia/Anaesthesia and Euthanasia of Animals

The rats were anaesthetized with an intraperitoneal injection of ketamine (100 mg/kg) and xylazine (5 mg/kg). A half dose of both anaesthetics was needed for the flash ERG recording of the rats. The rats were killed using a humane method (Scientific Procedures Acts 1986), namely an overdose (at least 140 mg/kg) of i.p. sodium pentobarbitone.

Induction of Retinal Ischaemia

The rats (200-250 g) were anaesthetized and placed in a stereotaxic frame. The anterior chamber of one eye was cannulated with a 30-gauge needle connected to a 0.9% saline reservoir; this caused a high IOP (HIOP) of 120 mmHg for 60 minutes. Eye fundus whitening and a low ERG response confirmed induction of an ischaemic insult. A sham procedure was carried out on the controls.

Drug Administration

Drug administration involved the pre-administration (15-minute before 60-minute HIOP induced retinal ischaemia) of SAC (25, 50, 100 µM) or vehicle (saline; control). The ischemic eye of each test rat was treated with or without a single intravitreous injection of 5 µl of the test compound. In addition, SAC (100 µM) was administered to the non-ischaemic eye (normal) to see whether SAC has any adverse effects. In both cases, the paired normal eye was untreated.

Recording of Flash ERG

Flash ERG recordings were performed on all rats before retinal ischaemia (day 0), as well as at 1, 3, 5, and 7 days after ischaemia and treatment with or without the defined chemicals. The animals were dark adapted and anaesthetized to do this. A strobe was placed 2 cm in front of the animal to provide a stimulus of 0.5 Hz. Fifteen consecutive responses were recorded at two-second intervals and at 10 kHz; the responses were amplified and averaged using an amplifier P511/regulated power supply RPS 107/stimulator PS22 (Grass-Telefactor; Astro-Med Inc., West Warwick, R.I., USA). For comparative purposes, the b-wave ratio, namely the b-wave amplitude of the ischaemic/sham-operation eye or the untreated/SAC-treated non-ischaemic (normal) eye as compared with that of the contralateral normal eye, was calculated.

Immunofluorescence Analysis

The rats were sacrificed and intracardially perfused with 0.9% normal saline (w/v). Then the rat retinas were removed, fixed with 4% (w/v) paraformaldehyde for 45 minutes and then transferred to 30% sucrose for cryosectioning. Sampling was carried out one or seven days after the sham-operation or induction of retinal ischaemia. The retinal sections from the eyes were incubated with primary antibody, namely goat anti-choline acetyltransferase (ChAT) polyclonal antibody (1:100; AB144p; Chemicon, Temecula, Calif., USA). Then the retinal sections were incubated with an appropriate secondary antibody, namely rhodamine-conjugated rabbit anti-goat antibody (1:500; AP106R; Chemicon, Temecula, Calif., USA). At the same time, the nuclei of the cells were labeled with 4,6-diamidine-2-phenylindole dihydrochloride (DAPI; 30 nM; Molecular Probes, Eugene, USA). The retinal sections were examined using a fluorescence microscope (Olympus BX61, Center Valley, Pa., USA).

Assessment of the Levels of Various Retinal mRNAs in the Retina by Real-time Polymerase Chain Reaction (PCR)

The levels of Thy-1, HIF-1 Alpha, VEGF and MMP-9 mRNAs present in the retinas were determined using a real-time PCR technique. Twenty four hours after retinal ischaemia and treatment with the defined chemicals or a sham-operation, the rats were killed and the retinas removed. This was followed by sonication in TriReagent (Sigma Chemical, St Louis, Mo., USA). Total retinal RNA was isolated and first strand complementary DNA (cDNA) synthesis was performed on 2 µg deoxyribonuclease (DNase)-treated RNA using High Capacity RNA-to-cDNA Master Mix. The first-strand cDNA then underwent real-time PCR using Fast SYBRR Green Master Mix. The PCR was initiated by incubation at 95° C. for 20 sec; then 40 cycles of 95° C. for 3 sec and 60° C. for 30 sec were performed. Cycling was carried out on a StepOnePlus™ Real-Time PCR System. Relative quantification (a comparative method) was performed using the house keeping gene Beta-actin as the internal standard. This process allows the normalized quantification of the mRNA target (Ct) and takes into account the differences in the amount of total RNA added to each reaction ($\Delta$Ct). The relative HIF-1 Alpha/VEGF/MMP-9 expression changes were calculated as fold changes relative to the control with respect to the calibrator ($\Delta\Delta$Ct), which was represented by the control retina. Relative quantification of gene expression was calculated according to the method $2^{-\Delta\Delta Ct}$, as described in the manufacturer's instructions, and was carried out by the accompanying software (RQ, ver. 1.3). The PCR reagents, software and machine were purchased from AB Applied Biosystems (Foster City, Calif., USA). The data obtained for each treatment were pooled, and a total percentage change relative to the control was calculated. The PCR oligonucleotide primers were obtained from MISSION BIOTECH (Taipei, Taiwan) as follows:

```
Beta-actin Forward:
                                    (SEQ ID No: 1)
5'-GAACCGCTCATTGCCGATAGTG-3';

Reverse:
                                    (SEQ ID No: 2)
5'-TTGTCCCTGTATGCCTCTGGTCG-3';

Thy-1 Forward:
                                    (SEQ ID No: 3)
5'-ACCAAGGATGAGGGCGACTA-3';

Reverse:
                                    (SEQ ID No: 4)
5'-CAGGCTTATGCCACCACACTT-3';

HIF-1 Alpha Forward:
                                    (SEQ ID No: 5)
5'-ACAGCTCCCCAGCATTTCAC-3';

Reverse:
                                    (SEQ ID No: 6)
5'-GGACAAACTCCCTCACCAAAAA-3';

VEGF Forward:
                                    (SEQ ID No: 7)
5'-GCGGGCTGCTGCAATG-3';

Reverse:
                                    (SEQ ID No: 8)
5'-TGCAACGCGAGTCTGTGTTT-3';

MMP-9 Forward:
                                    (SEQ ID No: 9)
5'-TGCGCTGGGCTTAGATCATT-3';

Reverse:
                                    (SEQ ID No: 10)
5'-TGGATGCCTTTTATGTCGTCTTC-3';
```

Cell Culture Studies

The RGC-5 cell line was obtained from the American Type Culture Collection (ATCC, No. CRL-2302, Manassas, Va., USA). The RGC-5 cell line represents a lineage of neuronal precursor cells. The RGC-5 cells were maintained in Dulbecco's modified Eagle's medium (DMEM; Falcon, Becton Dickinson, N.J., U.S.A.) containing 10% fetal calf serum, 100 U/mL penicillin and 100 µg/mL streptomycin (Sigma-Aldrich) in a humidified atmosphere of 95% air and 5% $CO_2$ at 37° C. Cell viability was evaluated by counting the cell number using a haemocytometer under an optical microscope.

In the enzyme-linked immunosorbent assay (ELISA), the cells ($2.5 \times 10^4$ in each well) were plated into 96-well plates. Each well contains 200 µl of DMEM (control) without or with $H_2O_2$. Next, the cells were incubated at 37° C. for 1 day and then shifted to serum free medium for the following day. In order to stimulate oxidative stress, 500 µM $H_2O_2$ (Sigma-Aldrich 18304/k0250, St Louis, Mo., USA) was then added for 24 hours as described elsewhere. Depending on the experimental protocol, SAC or vehicle was added to some samples 15 minutes before adding $H_2O_2$.

Enzyme-linked Immunosorbent Assay (ELISA)

Medium from the RGC-5 cell samples were collected and the cells separated by treating with trypsin-ethylenediaminetetraacetic acid (EDTA) from the culture plate twenty-four hours after $H_2O_2$ administration. The medium was assayed immediately or stored at $-20°$ C. until used. The cells were retrieved by centrifugation and washed three times in cold PBS. Freeze/thawing of the cells with gentle mixing using liquid nitrogen was carried out three times to induce lysis. Total protein was determined using a bicinchoninic acid protein kit (Thermo Fisher Scientific Inc., IL, U.S.A.).

The HIF-1 Alpha/VEGF/MMP-9 levels in the cells/medium were measured using various ELISA kits, namely HIF-1 Alpha (Uscn Life Science Inc., Wuhan 430056, China); VEGF-A (BMS277/2, Bender Medsystem, Vienna, Austria) and MMP-9 Duoset (D911, R&D, Minneapolis, Minn., U.S.A.). All ELISAs were carried out according to the manufacturer's instruction.

In brief, to measure the levels of HIF-1 Alpha or VEGF, a monoclonal anti-HIF-1 Alpha antibody or an anti-VEGF-A antibody had been previously coated onto the microwells. After washing, HIF-1 Alpha or VEGF-A in the samples was allowed to bind to the antibodies coated on the microwells for 2 hours at 37° C. or room temperature. After washing, 100 µl biotin-conjugated polyclonal anti-HIF-1 Alpha or monoclonal anti-VEGF-A antibody was added to each well for 1 hour. After washing to remove unbound biotin-conjugated anti-HIF-1 Alpha or anti-VEGF-A, 100 µl avidin-HRP or streptavidin-HRP was added and bound to the biotin-conjugated HIF-1 Alpha or anti-VEGF-A antibody. Following 30 minutes or 1 hour incubation, unbound avidin-HRP or streptavidin-HRP was removed by washing. Finally, 3,3',5,5'-tetramethylbenzidine (TMB; 100 µM) solution, which can be oxidised by HRP, was added to each well for twenty or thirty minutes and then 50 µl or 100 µl stop solution (phosphoric acid solution; 500 µM) was added to each well while measuring HIF-1 Alpha or VEGF respectively.

In brief, to measure the levels of MMP-9, each well of an ELISA 96-well plate was coated with 100 µl capture antibody (1 µg/ml) overnight, washed with 400 µl PBST twice, and blocked by 300 µl reagent diluent (1% BSA in PBS) for two hours. Next, after washing with PBST, the samples were added to each well and incubated at room temperature for two hours. After washing again with PBST, 100 µl detection antibody (200 ng/ml) and 100 µl streptavidin-HRP was added sequentially to each well, and incubated for two hours and twenty minutes, respectively. Finally, each well was incubated with 100 µl TMB (100 µM) for twenty minutes, and 50 µl 2N $H_2SO_4$ was added to stop the reaction.

The HIF-1 Alpha/VEGF/MMP-9 concentration of each sample was determined by constructing a standard curve using 100 µl of sample diluent containing various amounts of HIF-1 Alpha/VEGF/MMP-9 pure protein (0-1000 pg/ml). The instrument was adjusted to zero with 100 µl sample diluents, which served as blank. The absorbance (optical intensity, O.D.) was detected at 450 nm by spectrophotometer (ELx800, Biotek, Winooski, Vt., U.S.A.). The levels of HIF-1 Alpha/VEGF/MMP-9 in each sample were measured relative to each standard curve, and expressed as O.D. values relative to that of the control group (normalized to 100%).

Statistical Analysis

One-way analysis of variance (ANOVA) was performed to compare three or more independent groups. Following the one-way ANOVA, the Tukey multiple-comparison test was carried out to compare the control column (such as vehicle-treated ischaemic rats) with all other columns (such as SAC-treated ischaemic rats). All the results are shown as mean±standard error of the mean of the studied sample size (n=6). A p value of <0.05 was considered significant.

Results

The Effect of SAC on Retinal Electrophysiological Function

In the sham-operation eye (control; FIG. 1a), the ERG b-wave amplitude was measured (0.35 mV) as a control. When the IOP was raised to induce retinal ischaemia followed by reperfusion for 1 day (ischaemic eye), the b-wave amplitude was drastically reduced. This reduction was not affected by pre-treatment with vehicle [saline: 0.08 mV (22.86% of the control value)]. However, pre-treatment with SAC (100 µM) dramatically attenuated the ischaemia induced reduction in b-wave amplitude and raised the value to 0.24 mV (68.57% of the control value) 1 day after I/R.

In FIG. 1b (n=6), when compared to the pre-ischaemia b-wave ratio [baseline; day 0; 0.96±0.05 or 0.98±0.05 (figure not shown; n=6)], after I/R, there is a significant (p<0.05) reduction in the ERG b-wave ratio in the ischaemic eye (vs. the fellow normal eye) with or without pre-treatment with vehicle [(day 1, 0.10±0.02); (day 3, 0.13±0.02); (day 5, 0.14±0.02); (day 7, 0.13±0.03); figure not shown)]. Specifically, the reduced b-wave ratio in the ischaemic eye (vs. the fellow normal eye) that had been pre-treated with vehicle was irreversible and was similar on day 1 (0.19±0.03), 3 (0.18±0.05), 5 (0.24±0.05), or 7 (0.18±0.02) after I/R (induced by 60-minute HIOP). After pre-treated with SAC however, there was a concentration-dependent (25 µM vs. 50 µM vs. 100 µM) and significant (p<0.05; at 50 µM and 100 µM) improvement in the ischaemia induced reduction in b-wave amplitude (ratio) on the day 1 (0.47±0.10 vs. 0.56±0.03 vs. 0.64±0.04), day 3 (0.44±0.11 vs. 0.60±0.05 vs. 0.79±0.03), day 5 (0.54±0.09 vs. 0.65±0.02 vs. 0.84±0.03) or day 7 (0.55±0.06 vs. 0.61±0.05 vs. 0.84±0.04) after I/R. The pre-ischaemia b-wave ratio baseline (day 0) for each defined group pre-treated with SAC was also recorded [(1.08±0.07 at 25 µM; 0.98±0.04 at 50 µM; 0.92±0.04 at 100 µM]. Statistically, there is no significant difference between various groups. Similarly, when the ERG b-wave ratios of the non-treated normal eye (n=6) or the sham-operation eye (n=5) vs. the fellow normal eye were compared as controls [(1.00±0.0, baseline; 1.01±0.04, pre-sham operation; on day 0); (1.04±0.02 on day 1; 0.99±0.05 on post-operative day 1); (1.01±0.02 on day 3; 1.04±0.07 on post-operative day 3); (1.00±0.03 on day 5; 1.05±0.05 on post-operative day 5); (1.06±0.03 on day 7; 0.92±0.04 on post-operative day 7); figures not shown], there was also no significant difference between the ERG b-wave ratio at the baseline (day 0) and that on the day 1, 3, 5 or 7 after the baseline recording for the non-treated normal group or the sham operation group. Additionally, 100 µM SAC had no significant adverse effect on the b-wave amplitude (ratio) of the non-ischemic (normal) eye (vs. the fellow normal eye) on the day 0 (1.11±0.05), 1 (1.05±0.06), 3 (1,07±0.10), 5 (1.06±0.12), or 7 (0.91±0.09) after the administration of 100 µM SAC (n=3; figure not shown).

The Effect of SAC on ChAT Immunoreactivity

Figure 2:
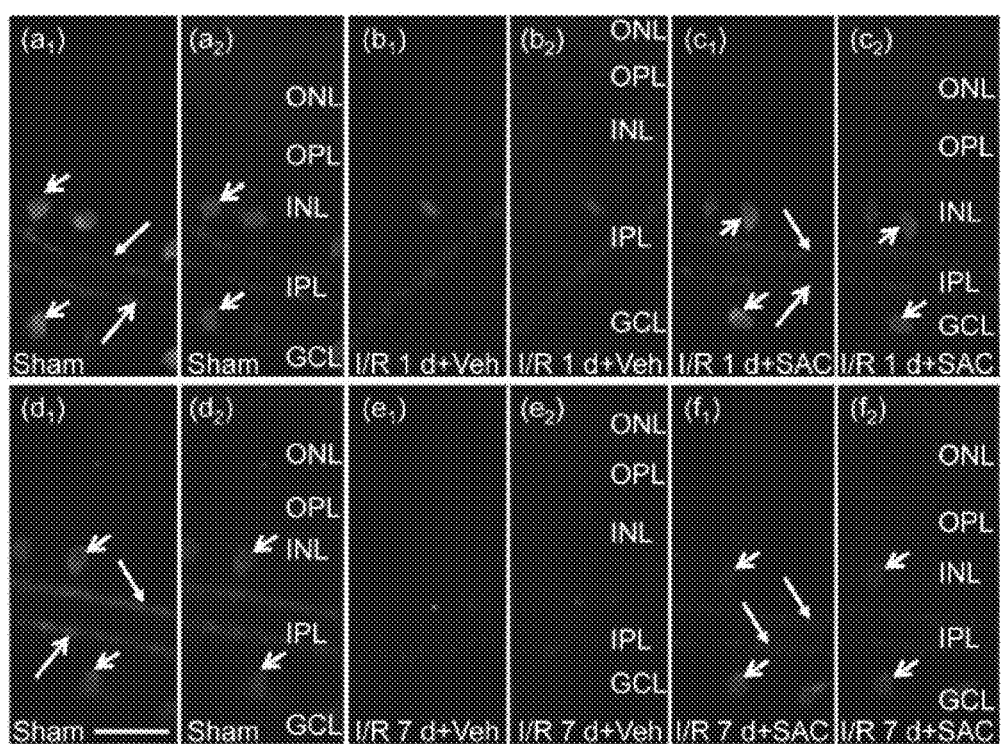
FIG. 2 shows choline acetyltransferase (ChAT) immunoreactivity (red) in the retina subjected to ischaemia followed by reperfusion (I/R) for 1 ($a_1$ and $a_2$; $b_1$ and $b_2$; $c_1$ and $c_2$) or 7 days ($d_1$ and $d_2$; $e_1$ and $e_2$; $f_1$ and $f_2$) after treatment with vehicle (0.9% saline) or 100 μM SAC, which were pre-administered 15 minutes before HIOP induced ischaemia. In the sham-operated retina (normal control: $a_1$ and $a_2$; $d_1$ and $d_2$), ChAT is associated with amacrine perikarya (short arrows) in the INL and GCL as well as their processes in the IPL, which are seen as two clearly defined strata of immunoreactivity (long arrows). I/R caused an almost complete obliteration of the ChAT immunoreactivity in the IPL and the number of ChAT immunopositive amacrine cell bodied was drastically reduced (figure not shown); the ischaemia induced alterations were not affected by pretreatment with vehicle ($b_1$ and $b_2$; $e_1$ and $e_2$). However, the effect of ischaemia/reperfusion was obviously nullified by pre-ischaemic intravitreous treatment with 100 μM SAC ($c_1$ and $c_2$; $f_1$ and $f_2$). The retinal cellular nuclei in different groups were respectively counterstained with DAPI (blue). The merge images of ChAT and DAPI labeling are shown in the pictures $a_2, b_2, c_2, d_2, e_2,$ and $f_2$. The abbreviations are: SAC, S-allyl L-cysteine; ONL, outer nuclear layer; OPL, outer plexiform layer; INL, inner nuclear layer; IPL, inner plexiform layer; GCL, ganglion cell layer; DAPI, 4,6-diamidine-2-phenylindole dihydrochloride; HIOP, high intraocular pressure. Scale bar=25 μm.

In FIG. 2, at 1 and 7 days after operation, when the sham-operation retina (control: $a_1$ and $a_2$/$d_1$ and $d_2$) are examined, ChAT immunoreactivity (red) is associated with the amacrine cell bodies (short arrows; 39±3/38±3 per field) that are found in the inner nuclear layer (INL) and the ganglion cell layer (GCL) and neuronal processes that can be seen as a two-band pattern in the inner plexiform layer (IPL; long arrows). In the ischaemic retina pretreated with vehicle, the immunolabeling of amacrine cell bodies disappeared after I/R for 1 and 7 days (14±1/10±5 per field), whereas the labeling in the IPL was still visible ($b_1$ and $b_2$; $e_1$ and $e_2$: one-band pattern) after I/R for 1 and 7 days. Furthermore, the effect of I/R was obviously counteracted by pre-treatment with 100 μM SAC ($c_1$ and $c_2$/$f_1$ and $f_2$; 26±2/24±5 amacrine cell bodies per field) and the result was a retina similar to the control. When the retinal cellular nuclei in the different groups were counterstained with DAPI (blue; $a_2$, $b_2$, $c_2$, $d_2$, $e_2$ and $f_2$).

The Effect of SAC on Thy-1, HIF-1 Alpha, VEGF or MMP-9 mRNA in the Retina

Figure 3:
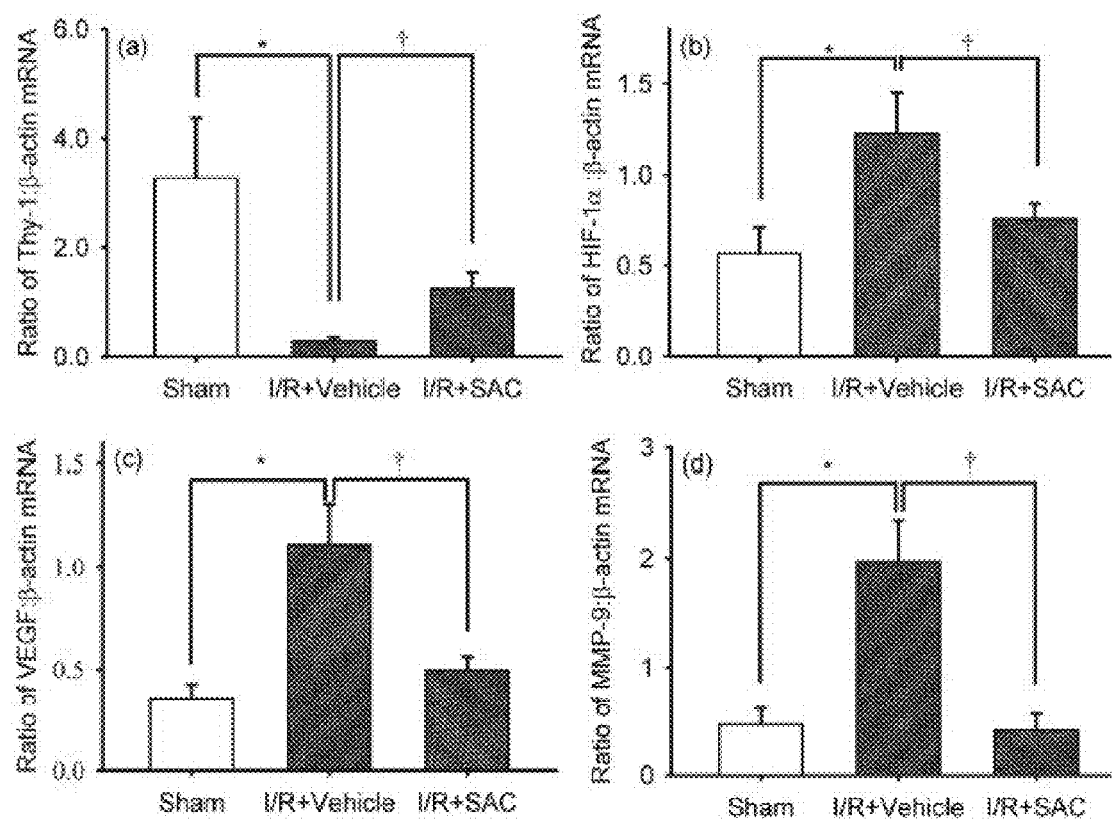
FIG. 3 shows real time polymerase chain reaction analysis measuring the expression of Thy-1 (a), HIF-1 Alpha (b), VEGF (c), MMP-9 (d) and β-actin. Twenty four hours after ischaemia plus reperfusion (I/R), whole retinal extracts were isolated from the sham-operated eyes (control) or the ischaemic eyes (subjected to 60-minute high intraocular pressure) pre-administered (15-minute before ischaemia) with intravitreous vehicle (0.9% saline), or 100 μM SAC. The effect of the either treatment on the Thy-1:β-actin mRNA ratio was shown compared to the control. β-actin is a house-keeping gene. */†, respectively, represents significant differences ($p<0.05$) between the vehicle-pretreated ischaemic group and the sham-operation group and between the vehicle-pretreated ischaemic group and the SAC-pretreated ischaemic group. The results are the mean±standard error of the mean for six animals (n=6). The abbreviations are: HIF-1 Alpha, hypoxia-inducible factor-1Alpha; VEGF, vascular endothelium growth factor; MMP-9, matrix metalloproteinase-9; SAC, S-allyl L-cysteine.

In FIG. 3 (n=6), as compared to the control retina [Thy-1 (3.28±1.09; a), HIF-1 Alpha (0.56±0.15; b), VEGF (0.36±0.07; c) and MMP-9 (0.46±0.15; d)], the ratios for Thy-1 (0.29±0.07; A), HIF-1 Alpha (1.23±0.23; B), VEGF (1.10±0.20; C) and MMP-9 (1.97±0.38; D) in the vehicle-pretreated ischaemic retina was significantly changed ($p<0.05$) after I/R.

When compared to the vehicle-pretreated ischaemic retina, the ischaemic retina pre-treated with 100 μM SAC [Thy-1 (1.25±0.30; a), HIF-1 Alpha (0.76±0.09; b), VEGF (0.50±0.06; c) and MMP-9 (0.41±0.15; d)] showed a significant ($p<0.05$) counteraction of the I/R induced Thy-1 decrease. This was complemented by a similar counteraction of the up-regulation of HIF-1 Alpha, VEGF and MMP-9.

The Effect of SAC on RGC-5 Cell Viability

Figure 4:
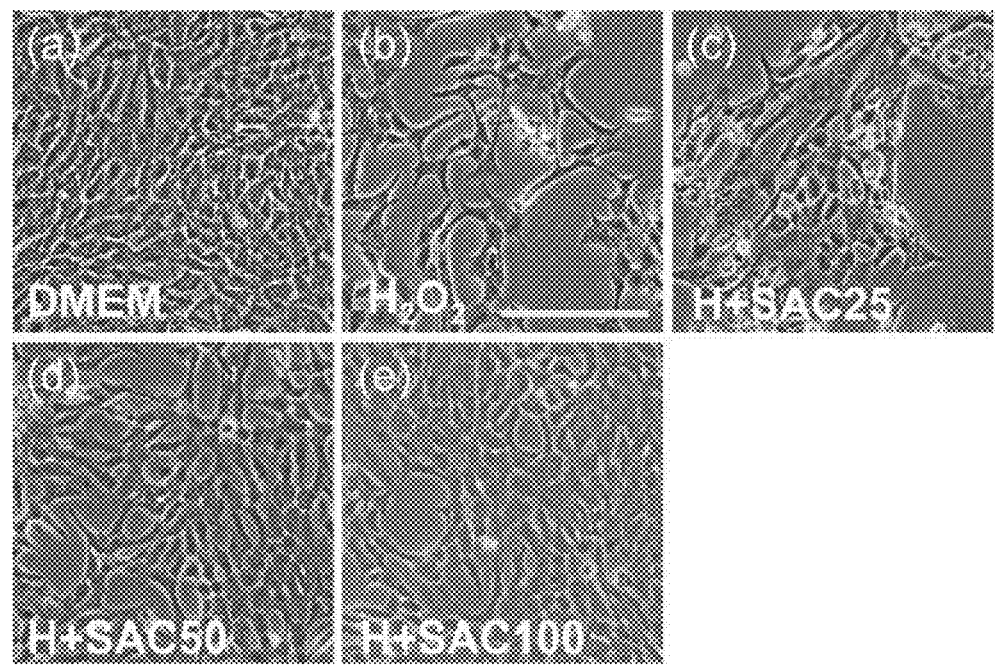
FIG. 4 shows the cell density as a representation of cell viability (observed by using optical microscopy). In the control group (a; RGC-5 cells cultured in DMEM), there were numerous RGC-5 cells. Furthermore, oxidative stress induced by incubation of the RGC-5 cells with 500 μM $H_2O_2$ (b) for 24 hours drastically reduced the number of RGC-5 cells. In contrast with picture b, but similar to picture a, pictures c, d and e indicate that 15-minute pre-incubation with 25 μM, 50 μM and 100 μM SAC resulted in a dose-dependent and obvious protection of the RGC-5 cells against the oxidative stress f. As compared to the RGC-5 cells cultured in DMEM (control), 24-hour incubation of RGC-5 cells with 500 μM $H_2O_2$ significantly (*$p<0.05$) reduced cell viability. As compared to the RGC-5 cells subjected to 24-hour $H_2O_2$ induced oxidative stress, 15-minute pre-incubation with 25 μM, 50 μM or 100 μM SAC dose-dependently and significantly (at 100 μM; †$p<0.05$) ameliorated the $H_2O_2$ induced significant (*$p<0.05$) decrease in cell viability. The results are the mean±standard error of the mean for six experiments (n=6). The abbreviations are: DMEM, Dulbecco's modified Eagle's medium; RGC-5, retinal ganglion cell-5; SAC, S-allyl L-cysteine; H, $H_2O_2$. Scale bar=50 μm.
Figure 4:
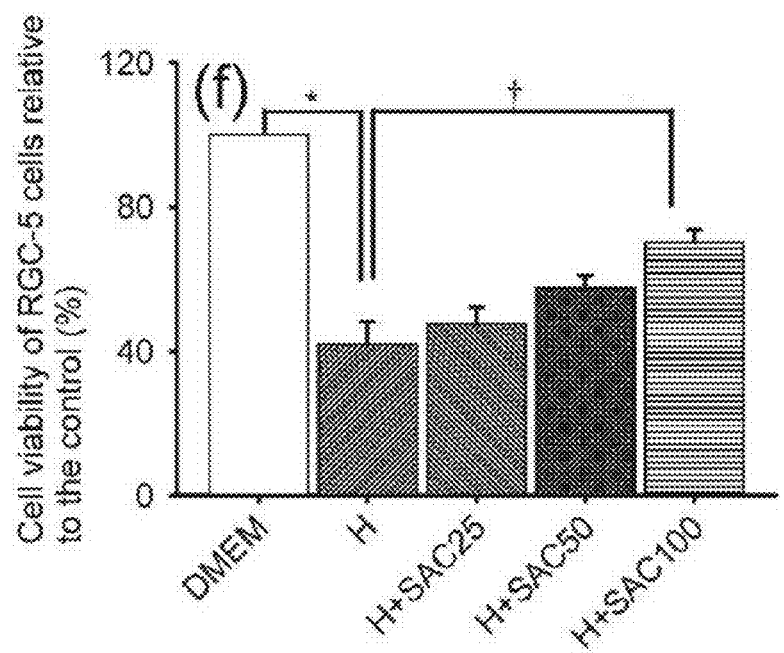

In FIG. 4, it can be seen that in the control (RGC-5 cells cultured in DMEM alone; a), there are numerous RGC-5 cells. However, after 24-hour incubation in the presence of 500 μM $H_2O_2$ there had been a significant reduction in the number of RGC-5 cells (b). However, a 15-minute pre-incubation with 25 μM (c), 50 μM (d) or 100 μM of SAC (e; greatest effect) concentration-dependently and obviously protected the RGC-5 cells against the subsequent oxidative stress.

Figure 5:
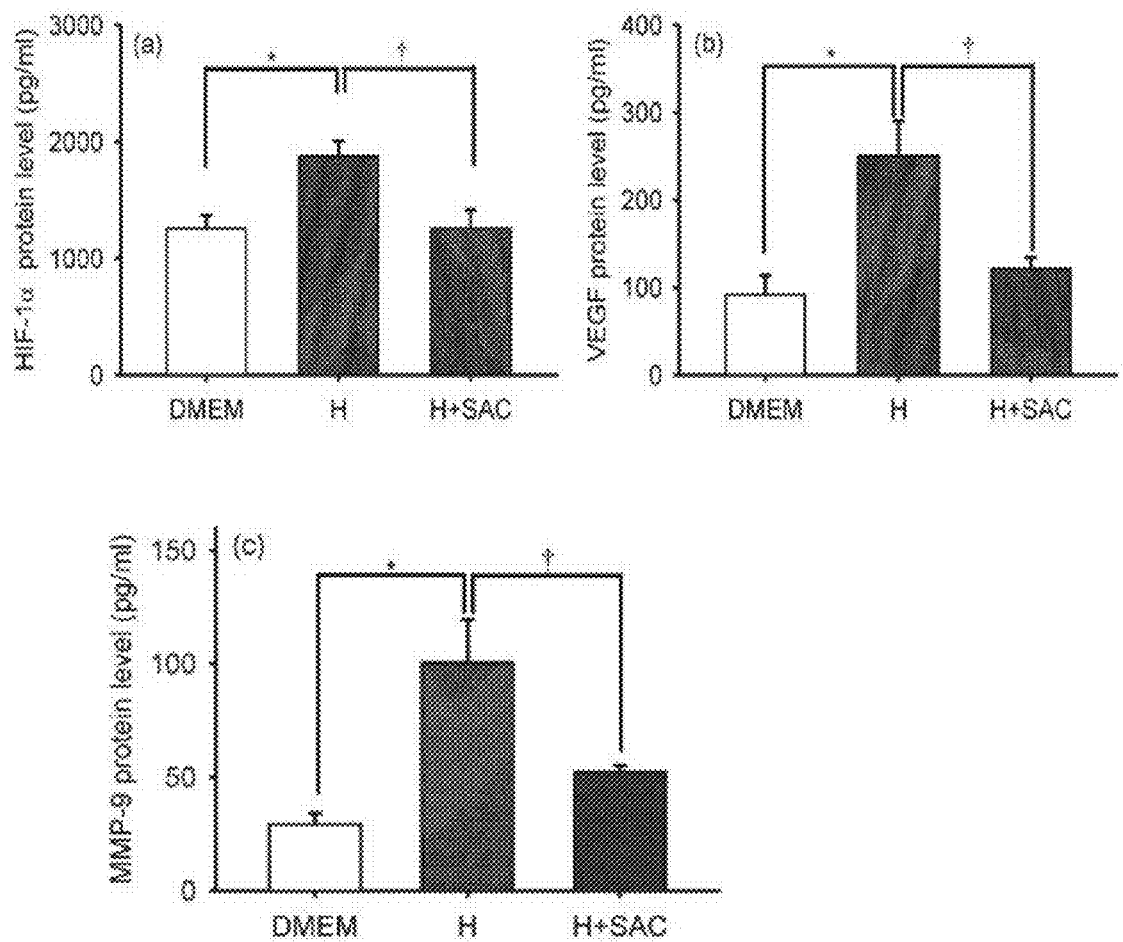
FIG. 5 shows the analysis of the expression of HIF-1 Alpha (a), VEGF (b) and MMP-9 (c) at the protein level. Twenty-four hours after 500 μM $H_2O_2$ induced oxidative stress, as compared to the RGC-5 cells incubated in DMEM (control), oxidative stress resulted in a significant (*$p<0.05$) up-regulation of HIF-1 Alpha, VEGF and MMP-9 protein levels. This significant (*$p<0.05$) up-regulation was significantly (†$p<0.05$) ameliorated by 15-minute pretreatment with 100 μM SAC. The results are the mean±standard error of the mean for six experiments (n=6). The abbreviations are: HIF-1 Alpha, hypoxia-inducible factor-1Alpha; VEGF, vascular endothelium growth factor; MMP-9, matrix metalloproteinase-9; RGC-5, retinal ganglion cell-5; DMEM, Dulbecco's modified Eagle's medium; SAC, S-allyl L-cysteine; H, $H_2O_2$.

In FIG. 5$f$ (n=6), as compared with the RGC-5 cells cultured in DMEM/F12 (control: 100%), after 24-hour incubation of RGC-5 cells with $H_2O_2$ (42.05±6.10%) there was a significant reduction ($p<0.05$) in cell viability. As compared with the RGC-5 cells subjected to defined oxidative stress, 15-minute pre-incubation with 25 μM (47.67±4.53%), 50 μM (57.51±3.48%) or 100 μM SAC (70.2±3.32%) concentration-dependently attenuated this decrease in cell viability. Furthermore, the significant adverse effect ($p<0.05$) of $H_2O_2$ was significantly ($p<0.05$) attenuated by pretreatment of the RGC-5 cells with 100 μM SAC.

The Effect of SAC on the Levels of HIF-1 Alpha, VEGF or MMP-9 Protein in the RGC-5 Cells In FIG. 5 (n=6), a concentration of 500 μM $H_2O_2$ was chosen to evaluate the expression of HIF-1 Alpha, VEGF or MMP-9 in the RGC-5 cells. As compared to the RGC-5 cells incubated in DMEM alone [control; HIF-1 Alpha (1254.39±116.03 pg/ml; a); VEGF (91.91±21.72 pg/ml; b); MMP-9 (29.33±4.93 pg/ml; c)], after 24-hour incubation of RGC-5 cells with $H_2O_2$, there was a significant ($p<0.05$) increase in the secretion of HIF-1 Alpha (1874.72±133.46 pg/ml), VEGF (250.55±39.63 pg/ml) and MMP-9 (100.70±18.80 pg/ml). Notably, this significant increase ($p<0.05$) was significantly attenuated ($p<0.05$) [HIF-1 Alpha (1256.47±157.62 pg/ml; a); VEGF (121.61±12.54 pg/ml; b); MMP-9 (52.55±2.72 pg/ml; c)] by 15-minute pre-treatment with SAC (100 μM).

One skilled in the art readily appreciates that the present invention is well adapted to carry out the objects and obtain the ends and advantages mentioned, as well as those inherent therein. The compounds, composition, processes and methods for producing them, and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating retina ischemia in a subject in need thereof, comprising administering to the subject a S-allyl-L-cysteine in a therapeutically effective amount, wherein the S-allyl-L-cysteine acts as an antioxidant.

2. The method of claim 1, wherein the S-allyl-L-cysteine attenuates the retina ischaemia induced reduction in electroretinogram b-wave amplitude.

3. The method of claim 1, wherein the S-allyl-L-cysteine attenuates the retina ischemia induced decrease in Thy-1 mRNA indexing retinal ganglion cells.

4. The method of claim 1, wherein the S-allyl-L-cysteine attenuates HIF-1 Alpha mRNA increase induced by the retina ischemia.

5. The method of claim 1, wherein the S-allyl-L-cysteine attenuates VEGF mRNA increase induced by the retina ischemia.

6. The method of claim 1, wherein the S-allyl-L-cysteine attenuates MMP-9 mRNA increase induced by the retina ischemia.

7. The method of claim 1, wherein the S-allyl-L-cysteine protects retinal ganglion cell-5 against oxidative stress.

8. The method of claim 7, wherein the oxidative stress is induced by $H_2O_2$.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial
<220> FEATURE:
<223> OTHER INFORMATION: Beta-actin forward primer for PCR
<220> FEATURE:
<221> NAME/KEY: misc_binding
<222> LOCATION: (1)..(22)

<400> SEQUENCE: 1
gaaccgctca ttgccgatag tg                                          22

```
<210> SEQ ID NO 2
<211> LENGTH: 23
<212> TYPE: DNA
<213> ORGANISM: Artificial
<220> FEATURE:
<223> OTHER INFORMATION: Beta-actin reverse primer for PCR
<220> FEATURE:
<221> NAME/KEY: misc_binding
<222> LOCATION: (1)..(23)

<400> SEQUENCE: 2
ttgtccctgt atgcctctgg tcg                                              23

<210> SEQ ID NO 3
<211> LENGTH: 20
<212> TYPE: DNA
<213> ORGANISM: Artificial
<220> FEATURE:
<223> OTHER INFORMATION: Thy-1 forward primer for PCR
<220> FEATURE:
<221> NAME/KEY: misc_binding
<222> LOCATION: (1)..(20)

<400> SEQUENCE: 3
accaaggatg agggcgacta                                                  20

<210> SEQ ID NO 4
<211> LENGTH: 21
<212> TYPE: DNA
<213> ORGANISM: Artificial
<220> FEATURE:
<223> OTHER INFORMATION: Thy-1 reverse primer for PCR
<220> FEATURE:
<221> NAME/KEY: misc_binding
<222> LOCATION: (1)..(21)

<400> SEQUENCE: 4
caggcttatg ccaccacact t                                                21

<210> SEQ ID NO 5
<211> LENGTH: 20
<212> TYPE: DNA
<213> ORGANISM: Artificial
<220> FEATURE:
<223> OTHER INFORMATION: HIF-1alpha forward primer for PCR
<220> FEATURE:
<221> NAME/KEY: misc_binding
<222> LOCATION: (1)..(20)

<400> SEQUENCE: 5
acagctcccc agcatttcac                                                  20

<210> SEQ ID NO 6
<211> LENGTH: 22
<212> TYPE: DNA
<213> ORGANISM: Artificial
<220> FEATURE:
<223> OTHER INFORMATION: HIF-1alpha reverse primer for PCR
<220> FEATURE:
<221> NAME/KEY: misc_binding
<222> LOCATION: (1)..(22)

<400> SEQUENCE: 6
ggacaaactc cctcaccaaa aa                                               22

<210> SEQ ID NO 7
<211> LENGTH: 16
<212> TYPE: DNA
<213> ORGANISM: Artificial
<220> FEATURE:
```

```
<223> OTHER INFORMATION: VEGF forward primer for PCR
<220> FEATURE:
<221> NAME/KEY: misc_binding
<222> LOCATION: (1)..(16)

<400> SEQUENCE: 7
gcgggctgct gcaatg                                                    16

<210> SEQ ID NO 8
<211> LENGTH: 20
<212> TYPE: DNA
<213> ORGANISM: Artificial
<220> FEATURE:
<223> OTHER INFORMATION: VEGF reverse primer for PCR
<220> FEATURE:
<221> NAME/KEY: misc_binding
<222> LOCATION: (1)..(20)

<400> SEQUENCE: 8
tgcaacgcga gtctgtgttt                                                20

<210> SEQ ID NO 9
<211> LENGTH: 20
<212> TYPE: DNA
<213> ORGANISM: Artificial
<220> FEATURE:
<223> OTHER INFORMATION: MMP-9 forward primer for PCR
<220> FEATURE:
<221> NAME/KEY: misc_binding
<222> LOCATION: (1)..(20)

<400> SEQUENCE: 9
tgcgctgggc ttagatcatt                                                20

<210> SEQ ID NO 10
<211> LENGTH: 23
<212> TYPE: DNA
<213> ORGANISM: Artificial
<220> FEATURE:
<223> OTHER INFORMATION: MMP-9 reverse primer for PCR
<220> FEATURE:
<221> NAME/KEY: misc_binding
<222> LOCATION: (1)..(23)

<400> SEQUENCE: 10
tggatgcctt ttatgtcgtc ttc                                            23
```